US009504757B2

(12) United States Patent
Kim et al.

(10) Patent No.: US 9,504,757 B2
(45) Date of Patent: Nov. 29, 2016

(54) SITE-SPECIFIC GLP-2 CONJUGATE USING AN IMMUNOGLOBULIN FRAGMENT

(71) Applicant: HANMI SCIENCE CO., LTD., Hwaseong-si, Gyeonggi-do (KR)

(72) Inventors: Seung Su Kim, Seoul (KR); Se Young Lim, Gunsan-si (KR); Sung Youb Jung, Suwon-si (KR); Se Chang Kwon, Seoul (KR)

(73) Assignee: HANMI SCIENCE CO., LTD., Hwaseong-Si (KR)

(*) Notice: Subject to any disclaimer, the term of this patent is extended or adjusted under 35 U.S.C. 154(b) by 0 days.

(21) Appl. No.: 14/369,436

(22) PCT Filed: Dec. 28, 2012

(86) PCT No.: PCT/KR2012/011748

§ 371 (c)(1),
(2) Date: Jun. 27, 2014

(87) PCT Pub. No.: WO2013/100704

PCT Pub. Date: Jul. 4, 2013

(65) Prior Publication Data

US 2014/0377290 A1 Dec. 25, 2014

(30) Foreign Application Priority Data

Dec. 30, 2011 (KR) ........................ 10-2011-0147684

(51) Int. Cl.
*A61K 38/26* (2006.01)
*A61K 47/48* (2006.01)

(52) U.S. Cl.
CPC ......... *A61K 47/48415* (2013.01); *A61K 38/26* (2013.01); *A61K 47/48215* (2013.01); *A61K 47/48369* (2013.01)

(58) Field of Classification Search
CPC . A61K 38/26; A61K 38/48; A61K 47/48215
See application file for complete search history.

(56) References Cited

U.S. PATENT DOCUMENTS 4,179,337 A 12/1979 Davis et al.
6,756,480 B2 6/2004 Kostenuik et al.
6,924,264 B1 8/2005 Prickett et al.
7,112,567 B2 9/2006 Bridon et al.
2007/0060512 A1 3/2007 Sadeghi et al.
2010/0105877 A1 4/2010 Song et al.

FOREIGN PATENT DOCUMENTS

CN 101646451 A 2/2010
KR 10-2008-0071134 A 8/2008
KR 10-2010-0105494 A 9/2010
KR 10-2012-0043205 A 5/2012
WO 02/46227 A2 6/2002
WO 2005/067368 A2 7/2005
WO 2006/076471 A2 7/2006
WO 2006/117565 A2 11/2006
WO 2008/082274 A1 7/2008
WO 2010/107256 A2 9/2010

OTHER PUBLICATIONS

Doherty et al., Bioconjug. Chem. 16: 1291-1298, 2005.*
Roberts et al,. Adv. Drug Del. Rev. 54: 459-476, 2002.*
European Patent Office, Communication dated Aug. 3, 2015 in counterpart European Application No. 12861579.6.
Bolette Hartmann et al., "In Vivo and in Vitro Degradation of Glucagon-Like Peptide-2 in Humans", The Journal of Clinical Endocrinology & Metabolism, 2000, pp. 2884-2888, vol. 85, No. 8.
D. G. Burrin et al., GLP-2 stimulates intestinal growth in premature TPN-fed pigs by suppressing proteolysis and apoptosis', Am J Physiol Gastrointest Liver Physiol, 2000, G1249-G1256, vol. 279.
K. Ljungmann et al., Time-dependent intestinal adaptation and GLP-2 alterations after small bowel resection in rats, Am J Physiol Gastrointest Liver Physiol, 2001, G779-G785, vol. 281.
Heather L. Cameron et al., "Glucagon-like peptide-2-enhanced barrier function reduces pathophysiology in a model of food allergy", Am J Physiol Gastrointest Liver Physiol, 2003, G905-G912, vol. 284.
Antonella Amato et al., "Glucagon-like peptide-2 relaxes mouse stomach through vasoactive intestinal peptide release", Am J Physiol Gastrointest Liver Physiol, 2009, G678-G684, vol. 296.
Qiang Xiao et al., "Circulating levels of glucagon-like peptide-2 in human subjects with inflammatory bowel disease", Am J Physiol Regulatory Integrative Comp Physiol, 2000, R1057-R1063, vol. 278.
Palle Bekker Jeppesen et al., "Glucagon-like Peptide 2 Improves Nutrient Absorption and Nutritional Status in Short-Bowel Patients With No Colon", Gastroenterology, 2001, pp. 806-815, vol. 120.
Juris J. Meier et al., "Glucagon-Like Peptide 2 Stimulates Glucagon Secretion, Enhances Lipid Absorption, and Inhibits Gastric Acid Secretion in Humans", Gastroenterology, 2006, pp. 44-54, vol. 130.
A. Tavakkolizadeh et al., "Glucagon-like Peptide 2: A New Treatment for Chemotherapy-Induced Enteritis", Journal of Surgical Research, 2000, pp. 77-82, vol. 91.

(Continued)

*Primary Examiner* — Gyan Chandra
(74) *Attorney, Agent, or Firm* — Sughrue Mion, PLLC

(57) ABSTRACT

Provided are a glucagon-like peptide-2 (GLP-2) conjugate containing native GLP-2 or its derivative and an immunoglobulin Fc fragment being covalently linked via a non-peptidyl polymer, wherein the native GLP-2 or its derivative has a thiol group introduced at its C-terminal end, and one end of the non-peptidyl polymer is linked to an amino acid residue of the GLP-2 other than the N-terminal amino group thereof; a method for preparing the GLP-2 conjugate; a pharmaceutical composition comprising the same; and a method for treating or preventing intestinal disease, intestinal injury, or gastrosis by using the same. Since the GLP-2 conjugate of the present invention has a remarkably increased binding affinity to a GLP-2 receptor, it shows a prolonged in vivo half-life and an improved in vivo durability and stability.

16 Claims, 5 Drawing Sheets

(56) References Cited

OTHER PUBLICATIONS

M Kumar et al., "Gene therapy of diabetes using a novel GLP-1/IgG1-Fc fusion construct normalizes glucose levels in db/db mice", Gene Therapy, 2007, pp. 162-172, vol. 14.

International Searching Authority, International Search Report of PCT/KR2012/011748 dated Apr. 10, 2013.

State Intellectual Property Office of the P.R.C.; Communication dated May 5, 2015 in counterpart application No. 201280071002.9.

"New glucagon like peptide useful in preparation of pharmaceutical composition for treating enteropathy,connected with immunoglobulin fragment crystallizable domain", Thompson Innovation, 2012-F64149/201275, Patent/Publication: KR2012043205A, Feb. 23, 2016, 5 pages total.

Daniel J. Drucker. Glucagon-Like Peptide 2. The Journal of Clinical Endocrinology & Metabolism, 2001, vol. 86, Issue 4, p. 1759-1764. Paragraphs 2 to 4 of left col. on p. 1761; third paragraph of left col. to first paragraph of right col. on p. 1762.

Communication dated Jun. 21, 2016, from the Intellectual Property Office of Taiwan in counterpart application No. 101150930.

* cited by examiner

| Test materials | $EC_{50}$ (nM) | Relative activity (% vs. GLP-2) |
|---|---|---|
| GLP-2 | 4.25 | 100 |
| LAPS-GLP2 | 49.22 | 8.6 |
| LAPS-DA GLP2 | 162.6 | 2.6 |
| LAPS-CA GLP2 | 56.82 | 7.5 |
| LAPS-OH GLP2 | 203.0 | 2.1 |
| LAPS-CA GLP2 (A2G, 34C) | 42.85 | 9.9 |

SITE-SPECIFIC GLP-2 CONJUGATE USING AN IMMUNOGLOBULIN FRAGMENT

TECHNICAL FIELD

The present invention relates to a glucagon-like peptide-2 (GLP-2) conjugate in which a GLP-2 or its derivative having a thiol group introduced at its C-terminal end is covalently linked to an immunoglobulin Fc fragment by a non-peptidyl polymer, wherein the non-peptidyl polymer and immunoglobulin Fc fragment are site-specifically linked to an amino acid residue of the GLP-2 or its derivative other than the N-terminal amino group thereof; a method for preparing the GLP-2 conjugate; a pharmaceutical composition comprising the same; and a method for treating or preventing intestinal disease, intestinal injury, or gastrosis by using the same.

BACKGROUND ART

Glucagon-like peptide-2 (GLP-2) is a 33 amino acid peptide hormone which is produced by the intestinal endocrine L cell upon nutrient ingestion. GPL-2 stimulates a mucosal growth in the small and large intestines (D G Burrin et al., Am J Physiol Gastrointest Liver Physiol 279(6): G1249-1256, 2000) and suppresses apoptosis of intestinal cells and crypt cells (Bernardo Yusta et al., Gastrpenterology 137(3): 986-996, 2009). Furthermore, GLP-2 enhances absorption of nutrients in the small intestine (PALLE B J et al., Gastrpenterology 120: 806-815, 2001) and reduces intestinal permeability (Cameron H L et al., Am J Physiol Gastrointest Liver Physiol 284(6): G905-12, 2003). In addition, GLP-2 suppresses gastric emptying and gastric acid secretion (Meier J J et al., Gastrpenterology 130(1): 44-54, 2006), while increasing an intestinal blood flow rate (Bremholm L et al., Scand J Gastroenterol. 44(3): 314-9, 2009) and relaxing intestinal smooth muscle (Amato A et al., Am J Physiol Gastrointest Liver Physiol. 296(3): G678-84, 2009).

Since GLP-2 has capabilities to absorb and protect energy and activate the function of intestinal cells, it has demonstrated a high therapeutic potential in various in vivo models of intestinal diseases and injuries. As a hormone for regulating nutrient absorption, GLP-2 has a therapeutic of great promise for the treatment of short bowel syndrome (SBS). SBS is caused by a congenital reason or an acquired reason such as the surgical removal of the intestine, and leads to nutritional deficiencies due to the decrease in the absorption area of the small intestine. It has been reported that GLP-2 improves nutrient uptake and absorption in the digestive tract in rat models having SBS (Ljungmann K et al., Am J Physiol Gastrointest Liver Physiol. 281(3): G779-85, 2001).

Further, Crohn's disease is a chronic inflammatory intestinal disease that can be caused in any region of the digestive tract ranging from the mouth to the anus. The cause of Crohn's disease is not yet known, but it is believed to be caused by an excessive inflammatory response of the body towards bacterial cells normally present within the digestive tract along with environmental and genetic reasons. It has been known that GLP-2 can prevent or relieve the damage in mucosal epithelial cells when mucositis, colitis or inflammatory intestinal disease is developed by chemotherapy or genetic reasons (Qiang Xiao et al., Am J Physiol Regul Integr Comp Physiol. 278(4): R1057-R1063, 2000).

Chemotherapy-induced diarrhea (CID) is one of the factors that limit the dose of an anticancer agent and is the most common side effect of anticancer chemotherapy. About 10% of the patients had advanced cancer. About 80% of the patients with advanced cancer received single/combination therapy of 5-FU (5-fluorouracil, Adrucil)/irinotecan (Camptosar) experience CID and about 30% of them show serious diarrhea symptoms of grade 3 to 5. In addition, if mucositis or neutropenia occurs simultaneously in the patients with CID, there is a possible risk of death. In the CID-induced rat models, GLP-2 shows the effect of alleviating the reduction of intestine weight, villus height and crypt depth that are induced by 5-FU, thereby demonstrating its therapeutic potential for CID treatment (A. Tavakkolizadeh et al., J Surg Res. 91(1): 77-82, 2000).

Despite this high therapeutic potential, GLP-2 still has limitations in being developed into a commercial drug. Peptides such as GLP-2 can be easily transformed due to low stability, are apt to be degraded by protease in the body and lose activity, and are easily removed through the kidney due to their relatively small size. Therefore, in order to maintain optimal blood concentrations and titers of peptide drugs, there is a need to administer the peptide drug more frequently. However, most peptide drugs are administered in various types of injections, and frequent injections are required to maintain the blood concentration of the peptide drug, which causes severe pain in patients. In this regard, there have been many attempts to solve these problems, one of which has developed a method of increasing membrane permeability of a peptide drug, leading to the delivery of the peptide drug to the body through an oral or a nasal route. But this method had a limitation of a low delivery efficiency of the peptide drug as compared with the injection thereof, and thus it still remains difficult to retain sufficient biological activity of the peptide drug for therapeutic use.

In particular, GLP-2 has extremely short in vivo half-life (7 minutes or shorter) due to its inactivation by dipeptidyl peptidase-IV (DPP IV) which cleaves between the amino acids at position 2 (Ala) and at position 3 (Asp) of GLP-2 (Bolette H. et al., The Journal of Clinical Endocrinology & Metabolism. 85(8): 2884-2888, 2000). It has been tried to increase the in vivo half-life of GLP-2 by amino acid substitution.

Currently, NPS Pharmaceuticals Inc. (U.S.A.) is developing as a therapeutic agent for Crohn's disease, SBS and gastrointestinal disease a GLP-2 analog "Teduglutide" in which the amino acid at position 2 (Ala) of native GLP-2 is substituted with asparagines (Asp). Teduglutide is resistant to the cleavage by DPPIV through the substitution of the amino acid at position 2, which in turn increases the stability and efficacy. However, since the increase in resistance to DPPIV cleavage is insufficient to extend the in vivo half-life of Teduglutide. Thus, Teduglutide also needs to be administered through injection once in a day, which is still a huge burden to the patient (WO 2005/067368).

Zealand Pharma (Denmark) is currently developing GLP-2 analogs by substitution of one or more amino acids at positions 3, 8, 16, 24, 28, 31, 32 and 33 of native GLP-2. These substitutions not only enhance the stability and efficacy of the peptide, but also allow for selective treatment of symptoms by making the growth promoting activity higher in the small intestine relative to in the colon depending on the position of substitution or vice versa. In addition, Zealand Pharma is developing Elsiglutide (ZP1846) as a GLP-2 analog targeting gastrointestinal (GI)-mucositis and CID, and Elsiglutide is undergoing in a Phase I clinical trial. However, the above analog also does not have sufficient in vivo half-life, and thus it needs to be administered through injection once a day (WO 2006/117565).

Polyethylene glycol (PEG) non-specifically binds to a specific site or various sites of a target peptide and increases the molecular weight thereof, thereby preventing renal clearance and hydrolysis of the target peptide without causing any side effect. For example, U.S. Pat. No. 4,179,337 describes a method of linking calcitonin with PEG to enhance in vivo half-life and membrane permeability of calcitonin. WO 2006/076471 describes a method for increasing in vivo half-life of a B-type natriuretic peptide (BNP), which has been used as a therapeutic agent for Congestive heart failure, by linking with PEG. In addition, U.S. Pat. No. 6,924,264 discloses a method for increasing in vivo half-life of exendin-4 by linking PEG with a lysine residue thereof. Although these methods can extend in vivo half-lives of the peptide drugs by increasing the molecular weight of PEG to be linked therewith, there are several problems in that as the molecular weight of PEG is increased, the titer of the peptide drug is reduced and the reactivity of PEG with the peptide drug is also decreased, leading to the reduction of yield.

WO 02/46227 describes a method for preparing a fusion protein of GLP-1, exendin-4 or an analog thereof with human serum albumin or an immunoglobulin Fc region. U.S. Pat. No. 6,756,480 also describes a method for preparing a fusion protein of a parathyroid hormone (PTH) or an analog thereof with an immunoglobulin Fc region. These methods can overcome the problems of pegylation such as low yield and non-specificity, but the effect of increasing in vivo half-lives of the drug peptide is not noticeable as expected, and sometimes the titers thereof are also still low. In order to maximize the effect of increasing in vivo half-life of a drug peptide, various kinds of peptide linkers can be used, but there is a risk of inducing an immune response. Further, if a peptide drug having a disulfide bond such as BNP is used, there is a high probability of misfolding. Finally, if a peptide drug including non-naturally occurring amino acids is employed, it is impossible to produce its fusion protein by genetic recombination.

In the previous study, the present inventors have developed a method for preparing a GLP-2 conjugate with extended in vivo half-life, in which the GLP-2 conjugate is prepared by covalently linking GLP-2 or its derivative to an immunoglobulin Fc fragment through a non-peptidyl polymer. In this method, the GLP-2 derivatives, such as beta-hydroxy-imidazo-propionyl GLP-2, where the N-terminal amine group of GLP-2 is substituted with a hydroxyl group, des-amino-histidyl GLP-2, where the N-terminal amine group thereof is deleted, and an imidazo-acetyl-GLP-2, where the alpha carbon of the first histidine and the N-terminal amine group linked thereto are deleted, showed increased resistance to DPPIV cleavage while maintaining their bioactivities and thus in vivo half-lives of the GLP-2 conjugates were remarkably increased.

However, in the case where the immunoglobulin Fc fragment was site-specifically linked to the lysine residue of these GLP-2 derivatives, thus obtained GLP-2 conjugates showed a significantly reduced binding affinity to GLP-2 receptor and thus had a problem in that in vivo efficacy and duration thereof would be reduced.

In this light of investigating a method that can increase in vivo half-life of GLP-2 in blood and maximize the duration of in vivo efficacy, the present inventors have developed a GLP-2 conjugate by conjugating a GLP-2 derivative into which a thiol group is introduced at the C-terminal thereof to a non-peptidyl polymer and an immunoglobulin Fc fragment by covalent linking, and found that the GLP-2 conjugate exhibits an increased binding affinity to GLP-2 receptor and a remarkably enhanced duration of in vivo efficacy. In particular, it has been found that when the non-peptidyl polymer and immunoglobulin Fc fragment are site-specifically linked to the cysteine residue introduced into the C-terminal end of an imidazo-acetyl-GLP-2 where the α-carbon of the first histidine and the N-terminal amine group linked thereto are deleted, leading to an increase in resistance to DPPIV, in vitro efficacy of the imidazo-acetyl-GLP-2 conjugate is significantly increased.

DISCLOSURE

Technical Problem

Accordingly, an object of the present invention is to provide a GLP-2 conjugate having enhanced in vivo therapeutic efficacy and stability.

Another object of the present invention is to provide a method for preparing the GLP-2 conjugate.

Still another object of the present invention is to provide a pharmaceutical composition comprising the GLP-2 conjugate as an active ingredient for the prevention or treatment of intestinal diseases, intestinal injuries, or gastrosis.

Technical Solution

In one aspect, the present invention provides a glucagon-like peptide-2 (GLP-2) conjugate comprising native GLP-2 or its derivative and an immunoglobulin Fc fragment being covalently linked via a non-peptidyl polymer, wherein the native GLP-2 or its derivative has a thiol group introduced at its C-terminal end, and one end of the non-peptidyl polymer is linked to an amino acid residue of the GLP-2 other than the N-terminal amino group thereof.

In another aspect, the present invention provides a method for preparing the GLP-2 conjugate according to the present invention, comprising:

1) covalently linking a non-peptidyl polymer having a reactive group selected from the group consisting of aldehyde, maleimide and succinimide derivatives at both terminal ends to an amine group or a thiol group of a GLP-2 or its derivative, wherein the GLP-2 or its derivative has a thiol group introduced at its C-terminal end;

2) isolating a complex, in which the non-peptidyl polymer is covalently linked to the amine group or thiol group of the GLP-2 or its derivative, from the reaction mixture of Step (1);

3) covalently linking the other end of the non-peptidyl polymer in the complex to an immunoglobulin Fc fragment; and 4) isolating a GLP-2 conjugate, in which both ends of the non-peptidyl polymer are linked to the immunoglobulin Fc fragment and GLP-2 or its derivative, respectively, from the reaction mixture of Step 3).

In still another aspect, the present invention provides a pharmaceutical composition comprising the GLP-2 conjugate according to the present invention as an active ingredient for preventing or treating one or more diseases selected from intestinal disease, intestinal injury and gastrosis.

In still yet another aspect, the present invention provides a method for preventing or treating one or more diseases selected from intestinal disease, intestinal injury and gastrosis, comprising administering the GLP-2 conjugate of the present invention to a patient in need thereof.

Advantageous Effects

The GLP-2 conjugate of the present invention has remarkably high binding affinity for a GLP-2 acceptor, thereby showing long-lasting in vivo therapeutic efficacy and prolonged in vivo half-life. Therefore, the GLP-2 conjugate of the present invention can be effectively used for the treatment or prevention of intestinal disease, intestinal injury or gastrosis with remarkably low administration frequency.

BEST MODE

Figure 1:
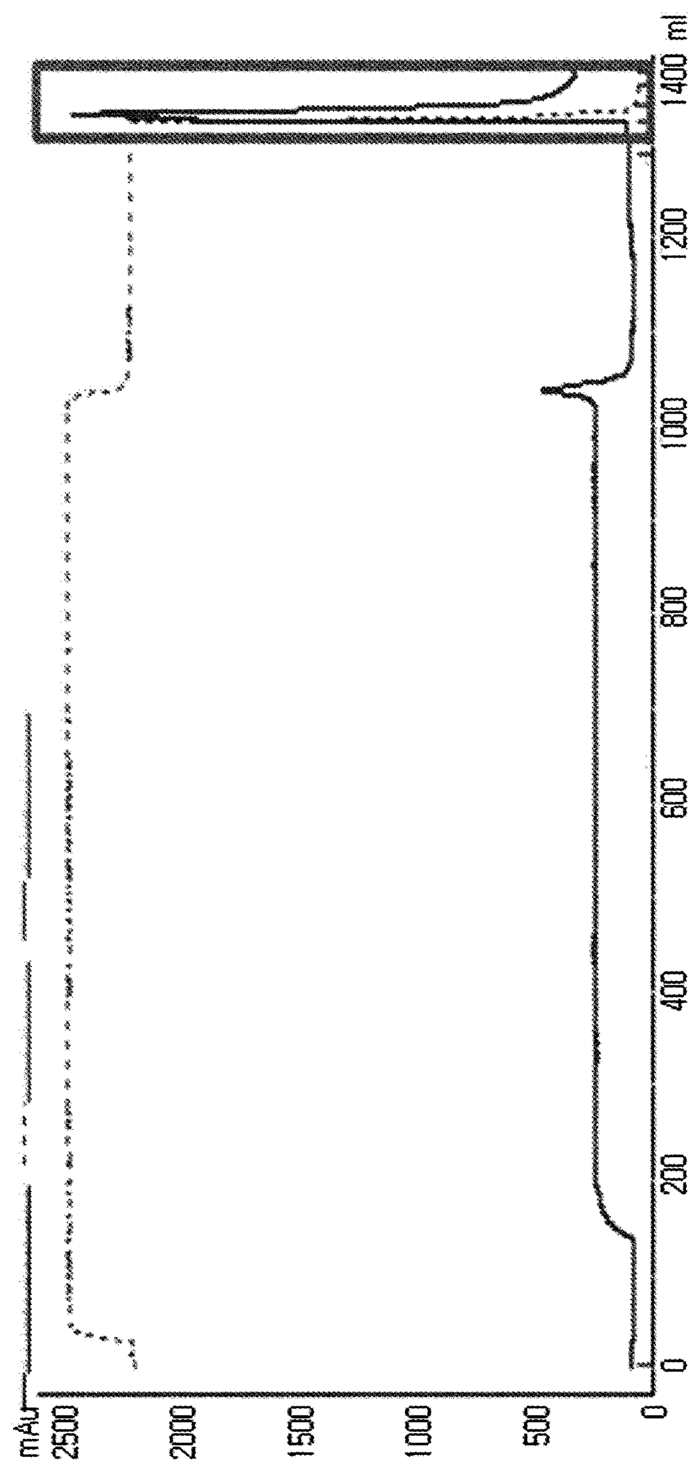
FIG. 1 shows the purification profile of a CA GLP-2(A2G, 34C)-10K PEG-immunoglobulin Fc conjugate, which is purified by using a Source Phe column.

In one aspect of the present invention, the present invention provides a glucagon-like peptide-2 (GLP-2) conjugate comprising a GLP-2 or its derivative and an immunoglobulin Fc fragment that are covalently linked by a non-peptidyl polymer, wherein the GLP-2 or its derivative has a thiol group introduced into its C-terminal end, and the non-peptidyl polymer is covalently linked to an amino acid residue of the GLP-2 or its derivative other than the N-terminal amino group thereof.

As used herein, the term "glucagon-like peptide-2 (GLP-2)" refers to a hormone which is secreted by the small intestine, generally promotes the biosynthesis and secretion of insulin, inhibits the secretion of glucagon, and promotes glucose absorption in the cells. GLP-2 has a function of treating or preventing intestinal disease, intestinal injury or gastrosis through the binding to a GLP-2 receptor. GLP-2 consists of 33 amino acids, the amino acid sequence of native GLP-2 being as follows:

```
GLP-2(1-33)
                                        (SEQ ID NO: 1)
HADGSFSDEMNTILDNLAARDFINWLIQTKITD
```

GLP-2 of the present invention includes a native form of GLP-2, its agonist, derivatives, fragments or variants and the like.

As used herein, the term "GLP-2 agonist" refers to a substance which can bind to a GLP-2 receptor regardless of its structural similarity to GLP-2 and induce the same or similar physiological activity as native GLP-2.

As used herein, the term "GLP-2 fragment" refers to a peptide having one or more amino acids added to or deleted from the N-terminal or C-terminal end of the native GLP-2, wherein the added amino acid can be a non-naturally occurring amino acid (e.g. D-amino acid).

In a preferred embodiment, GLP-2 of the present invention includes one having a thiol group introduced into its C-terminal end, wherein the thiol group can be introduced by adding a cysteine residue to the C-terminal end of GLP-2, but is not limited thereto.

As used herein, the term "GLP-2 variant" refers to a peptide having one or more amino acids different from that of native GLP-2. For this, the substitution with a non-naturally occurring amino acid as well as a naturally occurring amino acid can be induced.

As used herein, the term "GLP-2 derivative" refers to a peptide having at least 80% amino acid sequence homology as compared with that of native GLP-2, and to a peptide in which a portion of amino acid residues can be chemically substituted (e.g. alpha-methylation, alpha-hydroxylation), deleted (e.g. deamination), or modified (e.g. N-methylation). Preferably, the GLP-2 derivative of the present invention can be prepared by substitution, deletion, or modification of the N-terminal end of native GLP-2, and it can be selected from the group consisting of peptides, fragments and variants thereof possessing the function of GLP-2.

More preferably, the GLP-2 derivative of the present invention can be selected from the group consisting of:

an imidazo-acetyl-GLP-2 (CA-GLP2) where an e present invention can be selected from the group consisting of: log y as compared with that of native GLP-2, and to a reto are deleted;

a des-amino-histidyl GLP-2 (DA-GLP2) where an N-terminal amine group of native GLP-2 is deleted;

a beta-hydroxy-imidazo-propionyl GLP-2 (OH-GLP-2) where an N-terminal amine group of native GLP-2 is substituted with a hydroxyl group;

a dimethyl histidyl GLP-2 (DM-GLP-2) where an N-terminal amine group of native GLP-2 is modified to a dimethyl group; and a beta-carboxy-imidazo-propionyl GLP-2 (CX-GLP2) where an N-terminal amine group of native GLP-2 is substituted with a carboxyl group.

Even more preferably, the GLP-2 derivative can be a CA-GLP-2 where the α-carbon of the N-terminal first amino acid, histidine of native GLP-2 and the N-terminal amine group linked thereto are deleted.

In a preferred embodiment, GLP-2 or its derivatives of the present invention can be the peptide where a cysteine residue is introduced into the C-terminal end of native GLP-2, the α-carbon of the N-terminal end thereof and amine group linked thereto are deleted, and optionally, the second amino acid, alanine is substituted with glycine.

The native GLP-2 and GLP-2 derivatives according to the present invention can be synthesized using a solid phase synthesis method or recombination technology.

As used herein, the term "non-peptidyl polymer" refers to a biocompatible polymer including at least two repeating units that are linked to each other by any covalent bond other than a peptide bond. The non-peptidyl polymer suitable for the present invention can be selected form the group consisting of polyethylene glycol, polypropylene glycol, copolymers of ethylene glycol and propylene glycol, polyoxyethylated polyols, polyvinyl alcohol, polysaccharides, dextran, polyvinyl ethyl ether, biodegradable polymers such as polylactic acid (PLA) and polylactic-gly colic acid (PLGA), lipid polymers, chitins, hyaluronic acid and combinations thereof, and the preferred is polyethylene glycol. In addition, the scope of the non-peptidyl polymer in the present invention includes derivatives of the above listed polymers that are well known in the art or can be easily prepared by one skilled in the art.

Peptide linkers used in a fusion protein which is prepared by a conventional in-frame fusion method has the disadvantage that they can be easily cleaved by a proteolytic enzyme, and thus it is hard to obtain a significant increase in in vivo half-life of a physiologically active polypeptide due to the use of a carrier. However, the present invention employs a polymer having a resistance to such a proteolytic enzyme, and thus in vivo half-life of a physiologically active polypeptide can be maintained to be similar to that of a carrier.

Therefore, any non-peptidyl polymer can be used in the present invention without limitation as long as it is a polymer having a resistance to the proteolytic enzyme. The non-peptidyl polymer suitable for the present invention has a molecular weight in the range from 1 to 100 kDa, and preferably in the range from 1 to 20 kDa. Also, the non-peptidyl polymer of the present invention which is linked to the immunoglobulin Fc fragment may consist of one type of a polymer or combination of different types of polymers.

The non-peptidyl polymer of the present invention has a terminal reactive group that can bind to the immunoglobulin Fc fragment and the peptide drug at both ends thereof. The terminal reactive group at both ends of the non-peptidyl polymer is preferably selected from the group consisting of a reactive aldehyde group, a propionaldehyde group, a butyraldehyde group, a maleimide group and a succinimide derivative. The succinimide derivative may be exemplified by succinimidyl propionate, hydroxy succinimidyl, succinimidyl carboxymethyl, and succinimidyl carbonate. The terminal reactive groups at both ends of the non-peptidyl polymer may be the same or may be different to each other. For example, the non-peptide polymer may possess a maleimide group at one terminal thereof and an aldehyde group, a propionaldehyde group or a butyraldehyde group at the other terminal end thereof. In the case where polyethylene glycol (PEG) having a hydroxy group at both ends is used as a non-peptidyl polymer, the hydroxy group may be activated to various reactive groups through a conventional chemical reaction. In addition, commercially available PEG having a modified reactive group may be used to prepare the GLP-2 conjugate of the present invention.

In particular, when the non-peptidyl polymer having an aldehyde group at one end and a maleimide group at the other end is employed, it is possible to minimize non-specific reaction and to effectively induce the binding of the GLP-2 or its derivative and immunoglobulin Fc fragment to each end of the non-peptidyl polymer. A final product generated by an aldehyde bond through reductive alkylation is more stable than one generated by an amide bond. The aldehyde group selectively binds to the N-terminal end at low pH levels, but at high pH levels, such as pH 9.0, it binds to a lysine residue to form a covalent bond.

In a preferred embodiment, the non-peptidyl polymer of the present invention may have a maleimide group at one end and an aldehyde group at the other end, more preferably it may be a polyethylene glycol having a maleimide group at one end and an aldehyde group at the other end.

In the present invention, the immunoglobulin (Ig) Fc fragment is suitable for use as a drug carrier because it is biodegraded in vivo. Also, the Fc fragment is beneficial in terms of preparation, purification and yield of a complex with a peptide drug because it has a small molecular weight relative to whole immunoglobulin molecules. Further, since the Fab region, which displays high non-homogeneity due to the differences in amino acid sequences between antibodies, is removed, the Fc fragment has greatly increased substance homogeneity and a low potential to induce serum antigenicity.

The term "carrier," as used herein, refers to a substance linked to a drug. Typically, a complex comprising a drug linked to a carrier greatly decreases the physiological activity of the drug. However, with respect to the objects of the present invention, a carrier is employed in the present invention in order to minimize the decrease in physiological activity of a drug of interest, linked to the carrier, and reduce immunogenicity of the carrier, thereby enhancing in vivo stability of the drug. To accomplish these objects, the present invention employs an Fc fragment modified by a non-peptide polymer as a carrier.

As used herein, the term "immunoglobulin G (IgG)" collectively means a protein that participates in the body's protective immunity by selectively acting against antigens. Immunoglobulins are composed of two identical light chains and two identical heavy chains. The light and heavy chains comprise variable and constant regions. There are five distinct types of heavy chains based on differences in the amino acid sequences of their constant regions: gamma (γ), mu (μ), alpha (α), delta (δ) and epsilon (ϵ) types, and the heavy chains include the following subclasses: gamma 1 (γ1), gamma 2 (γ2), gamma 3 (γ3), gamma 4 (γ4), alpha 1 (α1) and alpha 2 (α2). Also, there are two types of light chains based on differences in the amino acid sequences of their constant regions: kappa (κ) and lambda (λ) types (Coleman et al., Fundamental Immunology, 2nd Ed., 1989, 55-73). According to the features of the constant regions of the heavy chains, immunoglobulins are classified into five isotypes: IgG, IgA, IgD, IgE and IgM. IgG is divided into IgG1, IgG2, IgG3 and IgG4 subclasses.

Immunoglobulins are known to generate several structurally different fragments, which include Fab, F(ab'), $F(ab')_2$, Fv, scFv, Fd and Fc. Among the immunoglobulin fragments, Fab contains the variable regions of the light chain and the heavy chain, the constant region of the light chain and the first constant region (CH1) of the heavy chain, and has a single antigen-binding site. The F(ab') fragments differ from the Fab fragments in terms of having the hinge region containing one or more cysteine residues at the C-terminal end (carboxyl terminus) of the heavy chain CH1 domain. The $F(ab')_2$ fragments are produced as a pair of the F(ab') fragments by disulfide bonding formed between cysteine residues of the hinge regions of the F(ab') fragments. Fv is the minimum antibody fragment that contains only the heavy-chain variable region and the light-chain variable region. The scfv (single-chain Fv) fragments comprise the heavy-chain variable region and the light-chain variable region that are linked to each other by a peptide linker and thus are present in a single polypeptide chain. Also, the Fd fragments comprise only the variable region and CH1 domain of the heavy chain.

As used herein, the term "immunoglobulin Fc fragment" is produced when an immunoglobulin (Ig) molecule is digested with papain, and is a region of an immunoglobulin molecule except for the variable region ($V_L$) and the constant regions (CO of the light chain and the variable region ($V_H$) and the constant region 1 ($C_H1$) of the heavy chain. The Fc fragment may further include the hinge region at the heavy-chain constant region. Also, the Fc fragment may be substantially identical to a native form, or may be an extended Fc fragment that contains a portion or the whole of the heavy-chain constant region 1 ($C_H1$) and/or the light-chain constant region 1 ($C_L1$) as long as it has an improved effect. In addition, the Fc fragment may be a fragment having a deletion in a relatively long portion of the amino acid sequence of $C_H2$ and/or $C_H3$. A preferred Fc fragment is an IgG or IgM-derived Fc fragment. An IgG-derived Fc fragment is more preferred, and IgG2 Fc and IgG4 Fc fragments are particularly preferred.

The Fc fragment modified according to the present invention may be a combination or hybrid of Fc fragments derived from IgG, IgA, IgD, IgE and IgM. The term "combination" means a dimeric or multimeric polypeptide in which single-chain Fc fragments of the same origin are linked to a single-chain Fc fragment of a different origin to form a dimer or multimer. The term "hybrid" means a polypeptide in which two or more domains of different origin are present in a single-chain Fc fragment. For example, a hybrid may be composed of one to four domains selected from among CH1, CH2, CH3 and CH4 domains contained in IgG1 Fc, IgG2 Fc, IgG3 Fc and IgG4 Fc.

The Fc fragment modified according to the present invention may be derived from humans or other animals including cows, goats, swine, mice, rabbits, hamsters, rats and guinea pigs, and preferably humans. The human-derived Fc fragment is preferable to a non-human derived Fc fragment, which may act as an antigen in the human body and cause undesirable immune responses such as the production of a new antibody against the antigen.

The Fc fragment modified according to the present invention includes a native amino acid sequence and sequence mutants (variants) thereof. An "amino acid sequence mutant" means to have a different sequence due to a deletion, an insertion, a non-conservative or conservative substitution or combinations thereof of one or more amino acid residues of a native amino acid sequence. Amino acid exchanges in proteins and peptides which do not generally alter the activity of the proteins or peptides are known in the art (H. Neurath, R. L. Hill, The Proteins, Academic Press, New York, 1979). The most commonly occurring exchanges are Ala/Ser, Val/Ile, Asp/Glu, Thr/Ser, Ala/Gly, Ala/Thr, Ser/Asn, Ala/Val, Ser/Gly, Thy/Phe, Ala/Pro, Lys/Arg, Asp/Asn, Leu/Ile, Leu/Val, Ala/Glu and Asp/Gly, in both directions. In addition, the Fc fragment, if desired, may be modified by phosphorylation, sulfation, acrylation, glycosylation, methylation, farnesylation, acetylation, amidation, and the like.

The amino acid variant may be a functional equivalent having biological activity identical to a native protein, or, if desired, may be made by altering the property of the native form. For example, the variant may have increased structural stability against heat, pH, etc., or increased solubility alteration and modification of the native amino acid sequence thereof. For example, in an IgG Fc fragment, amino acid residues known to be important in binding, at positions 214 to 238, 297 to 299, 318 to 322, or 327 to 331, may be used as a suitable target for modification. In addition, other various derivatives are possible, including one in which a region capable of forming a disulfide bond is deleted, or certain amino acid residues are eliminated at the N-terminal end of a native Fc form or a methionine residue is added thereto. Further, to remove effector functions, a deletion may occur in a complement-binding site, such as a C1q-binding site and an ADCC site. Techniques of preparing such sequence derivatives of the immunoglobulin Fc fragment are disclosed in International Patent Publication Nos. WO97/34631 and WO96/32478 and the like.

The Fc fragment modified according to the present invention may be obtained from a native form isolated from human and other animals, or may be obtained from transformed animal cells or microorganisms by the recombinant techniques.

The Fc fragment modified according to the present invention may be in the form of having native sugar chains, increased sugar chains compared to a native form, or decreased sugar chains compared to the native form, or may be in a deglycosylated form. A glycosylated Fc fragment has a high risk of inducing immune responses due to its stronger complement-dependent cytotoxicity (CDC) activity than an aglycosylated form. Thus, with respect to the present objects, an aglycosylated or deglycosylated Fc fragment is preferred.

As used herein, the term "deglycosylated Fc fragment" refers to an Fc fragment in which sugar moieties are artificially removed and the term "aglycosylated Fc fragment" means an Fc fragment that is produced in an unglycosylated form by a prokaryote, preferably *E. coli*. The increase, decrease, or removal of sugar chains of the Fc fragment may be achieved by methods common in the art, such as a chemical method, an enzymatic method and a genetic engineering method using a microorganism.

A recombinant Fc fragment has increased enzyme sensitivity due to the difference in the three dimensional structure from its native form. Also, an aglycosylated IgG is highly sensitive to proteolytic enzymes (pepsin, chymotrypsin) when compared to the native IgG (Morrison et al., J. Immunology 143: 2595-2601, 1989). A recombinant Fc fragment has the same binding affinity to FcRn as does the native Fc produced by papain treatment, but the native Fc fragment has a serum half-life 2 to 3 times longer than that of the recombinant Fc fragment (Eur. J. Immunology 29: 2819-2825, 1999). In the Fc fragment modified according to the present invention, an enzyme cleavage site is protected by a non-peptide polymer. This protection prevents the Fc fragment from being highly sensitive to hydrolases and having reduced in vivo half-life.

GLP-2 used in the present invention can be linked to the non-peptidyl polymer at various sites. When GLP-2 is linked to the site other than the N-terminal end which is important for physiological activity of the peptide, a reactive thiol group can be introduced into the amino acid residue to be modified in the amino acid sequence of native GLP-2 and a covalent bond can then be formed between the thiol group of GLP-2 and a maleimide group or an aldehyde group of the non-peptidyl polymer.

When the aldehyde group of the non-peptidyl polymer is used, it can react with an amino group at the N-terminal or the lysine residue. At this time, a modified form of GLP-2 can be used to selectively increase the reaction yield. For example, it is possible to maintain only one amine group capable of reacting with the non-peptidyl polymer at the desired site by protecting the N-terminal end of GLP-2, substituting the lysine residue with other amino acid, and introducing an amine group into the C-terminal end thereof, thereby increasing the yield of pegylation and coupling reaction. The methods for protecting the N-terminal end may include dimethylation, methylation, deamination, acetylation and the like, but are not limited thereto.

In a preferred embodiment of the present invention, in order to induce selective pegylation at the C-terminal amino acid residue of GLP-2, a cysteine residue is introduced into the C-terminal end of a GLP-2 derivative, and PEG having a maleimide group is then linked to the C-terminal cysteine residue of GLP-2. In particular, it has been found that the GLP-2 conjugate, in which an immunoglobulin Fc fragment is site-specifically linked to the C-terminal end of an imidazo-acetyl-GLP-2 (CA-GLP-2) whose alpha carbon of the first histidine and N-terminal amine group linked thereto are deleted, exhibits an improved binding affinity to a GLP-2 receptor as compared with a long-lasting GLP-2 derivative in which an immunoglobulin Fc fragment is linked to an original lysine residue (see FIG. 5).

In another embodiment, the present invention provides a method for preparing a GLP-2 conjugate, comprising the steps of:

1) covalently linking a non-peptidyl polymer having a reactive group at both ends thereof to an amine group or a thiol group of native GLP-2 or its derivative, wherein the reactive group is selected from the group consisting of aldehyde, maleimide, and succinimide derivatives, and wherein the thiol group is introduced into the C-terminal end of GLP-2 or its derivative;

2) isolating a complex comprising the non-peptidyl polymer and GLP-2 or its derivative from the reaction mixture of step 1), in which the non-peptidyl polymer is covalently linked to an amino acid residue other than an N-terminal amino group of GLP-2 or its derivative; and 3) covalently linking an immunoglobulin Fc fragment to the other end of the non-peptidyl polymer of the complex isolated in step 2), to thereby produce a GLP-2 conjugate comprising the immunoglobulin Fc region, non-peptidyl polymer and GLP-2 or its derivative, in which one end of the non-peptidyl polymer is covalently linked to the immunoglobulin Fc fragment and the other end thereof is covalently linked to GLP-2 or its derivative.

As used herein, the term "complex" refers to an intermediate between the non-peptidyl polymer and GLP-2 derivative that are covalently linked to each other. Subsequently, the other end of the non-peptidyl polymer that is not linked to the GLP-2 derivative is linked to the immunoglobulin Fc fragment.

Step (1) is to covalently link the GLP-2 or its derivative to one end of the non-peptidyl polymer. Preferably, the GLP-2 or its derivative may be a native GLP-2 having the amino acid sequence of SEQ ID NO: 1 or its N-terminal derivatives having a thiol group which is introduced into the C-terminal end of the GLP-2 or its derivative. Preferably, the GLP-2 derivative can be a CA-GLP-2, a DA-GLP2, an OH-GLP2, a DM-GLP-2, or a CX-CLP-2. More preferably, the GLP-2 derivative can be a CA-GLP-2 in which a cysteine residue is introduced into the C-terminal end thereof.

In Step 1), the reactive group at both ends of the non-peptidyl polymer can be the same or different. Preferably, one end of the non-peptidyl polymer may possess a maleimide group and the other end thereof may have an aldehyde group.

Furthermore, the non-peptidyl polymer in Step 1) is covalently linked to an amino acid residue of the GLP-2 or its derivative other than the N-terminal end thereof, preferably a thiol group of the cysteine residue introduced into the C-terminal of the GLP-2 or its derivative. For selective site-specific linking of the non-peptidyl polymer to the thiol group of the GLP-2 or its derivative, the reaction between the GLP-2 or its derivative and the non-peptidyl polymer in Step 1) can be performed at pH 2 to 4, preferably at pH 3. At this time, the molar ratio of the GLP-2 or its derivative to the non-peptidyl polymer in this reaction can be in a range from 1:2 to 1:10, but is not limited thereto.

The reaction of Step 1) can be performed in the presence of a reducing agent depending on the type of the reactive group at both ends of the non-peptidyl polymer, if necessary. The reducing agent suitable for the reaction may include sodium cyanoborohydride ($NaCNBH_3$), sodium borohydride, dimethylamine borate or pyridine borate.

Step 2) is to isolate the complex of GLP-2-non-peptidyl polymer, in which the GLP-2 or its derivative is covalently linked to one end of the non-peptidyl polymer, from the reaction mixture of Step 1). Considering physical properties such as purity, a molecular weight and a net charge of a target protein, the isolation of Step 2 can be conducted by appropriately selecting a conventional method known in the art for protein purification and isolation. For example, various conventional methods including size exclusion chromatography and ion exchange chromatography can be used and, if necessary, they can be combined for increasing the yield of a purified target product.

Step 3) is to carry out the reaction between the complex (GLP-2-non-peptidyl polymer) isolated in Step 2) and the immunoglobulin Fc fragment, to thereby covalently link the immunoglobulin Fc fragment to the other end of the non-peptidyl polymer included in the complex.

In Step 3), the reaction between the complex of GLP-2-non-peptidyl polymer and the immunoglobulin Fc fragment can be conducted at pH 5.0 to 8.0, preferably at pH 6.0. At this time, the molar ratio of the complex of GLP-2-non-peptidyl polymer to the immunoglobulin Fc fragment in this reaction can be in a range from 1:2 to 1:10, preferably 1:4 to 1:8.

The reaction of Step 3) can be performed in the presence of a reducing agent depending on the type of the reactive group at both ends of the non-peptidyl polymer, if necessary. The reducing agent suitable for the reaction may include sodium cyanoborohydride (NaCNBH3), sodium borohydride, dimethylamine borate, or pyridine borate.

In a preferable embodiment, the method for preparing a GLP-2 conjugate according to the present invention comprises the following step of:

1) covalently linking a non-peptidyl polymer having a maleimide group at one end and an aldehyde group at the other end to a thiol group of native GLP-2 or its derivative, and wherein the thiol group is introduced into the C-terminal end thereof;

2) isolating a complex comprising the non-peptidyl polymer and GLP-2 or its derivative from the reaction mixture of Step 1), in which the non-peptidyl polymer is covalently linked to the thiol group of GLP-2 or its derivative; and 3) covalently linking an immunoglobulin Fc fragment to the other end of the non-peptidyl polymer of the complex isolated in Step 2), to thereby produce a GLP-2 conjugate comprising the immunoglobulin Fc region, non-peptidyl polymer and GLP-2 or its derivative, in which one end of the non-peptidyl polymer is covalently linked to the immunoglobulin Fc fragment and the other end thereof is covalently linked to GLP-2 or its derivative.

In still another aspect, the present invention provides a pharmaceutical composition comprising the GLP-2 conjugate as an active ingredient.

The pharmaceutical composition of the present invention can be used for the prevention or treatment of one or more diseases selected from intestinal disease, intestinal injury, and gastrosis. Especially, the pharmaceutical composition of the present invention can be used for the prevention or treatment of the diseases including, but not limited to, GI disease including SBS, inflammatory bowel disease (IBD), Crohn's disease, colitis, pancreatitis, ileitis, inflammatory ileus, mucositis caused by cancer chemotherapy and/or radiotherapy, gastric atrophy caused by total parenteral nutrition or ischemia, bone impairment, pediatric gastrointestinal (GI) disorders including intestinal failure inducing newborn necrotic enteritis, and the like.

As used herein, the term "prevention" or "preventing" is intended to encompass all actions for restraining or delaying occurrence or progress of the above mentioned diseases such as intestinal disease, intestinal injury and gastrosis disease through administration of the pharmaceutical composition of the present invention.

The term "treatment" or "treating" in this context encompasses all actions for improving or beneficially changing symptoms of the above mentioned diseases such as intestinal disease, intestinal injury and gastrosis disease through administration of the pharmaceutical composition of the present invention.

The pharmaceutical composition of the present invention comprises as an active ingredient the long-lasting GLP-2 conjugate with an extended in vivo half-life and an improved in vivo efficacy and stability according to the present invention, and thus it can considerably reduce the administration dose of the drug and exhibit improved drug compliance without fluctuation in the blood glucose level. Therefore, the pharmaceutical composition of the present invention can be effectively used for preventing and treating intestinal disease, intestinal injury, or gastrosis.

The pharmaceutical composition of the present invention can further comprise a pharmaceutically acceptable carrier. For oral administration, the pharmaceutically acceptable carrier may include a binder, a lubricant, a disintegrator, an excipient, a solubilizer, a dispersing agent, a stabilizer, a suspending agent, a coloring agent and a perfume. For injectable administration, the pharmaceutically acceptable carrier may include a buffering agent, a preserving agent, an analgesic, a solubilizer, an isotonic agent and a stabilizer. For topical administration, the pharmaceutically acceptable carrier may include a base, an excipient, a lubricant, and a preserving agent.

The pharmaceutical composition of the present invention may be formulated into a variety of dosage forms in combination with the aforementioned pharmaceutically acceptable carriers. For example, for oral administration, the pharmaceutical composition may be formulated into tablets, troches, capsules, elixirs, suspensions, syrups or wafers. For injectable administration, the pharmaceutical composition may be formulated into an ampule as a single-dose dosage form or a unit dosage form, such as a multidose container. The pharmaceutical composition may be also formulated into solutions, suspensions, tablets, pills, capsules and long-acting preparations.

On the other hand, examples of the carrier, excipient and diluent suitable for the pharmaceutical composition of the present invention may include lactose, dextrose, sucrose, sorbitol, mannitol, xylitol, erythritol, maltitol, starch, acacia rubber, alginate, gelatin, calcium phosphate, calcium silicate, cellulose, methylcellulose, microcrystalline cellulose, polyvinyl pyrrolidone, water, methyl hydroxybenzoate, propyl hydroxybenzoate, talc, magnesium stearate and mineral oils. In addition, the pharmaceutical composition of the present invention may further include fillers, anti-coagulating agents, lubricants, humectants, perfumes and antiseptics.

The pharmaceutical composition of the present invention may be administered via any one of the common routes, as long as it is able to reach a desired tissue. A variety of modes of administration are contemplated, including intraperitoneally, intravenously, intramuscularly, subcutaneously, intradermally, orally, topically, intranasally, intrapulmonarily and intrarectally, but are not limited thereto.

However, since peptides are digested upon oral administration, the effective ingredient of the pharmaceutical composition for oral administration should be coated or formulated for protection against degradation in the stomach. Preferably, the pharmaceutical composition of the present invention may be administered in an injectable form. In addition, the pharmaceutical composition of the present invention may be administered using a certain apparatus capable of transporting the effective ingredient into a target cell.

The administration frequency and dose of the pharmaceutical composition of the present invention can be determined by several related factors including the types of diseases to be treated, administration routes, the patient's age, gender, weight and severity of the illness, as well as by the types of the drug as an effective ingredient. However, the dose may be increased or decreased according to the route of administration, the severity of disease, and patient's sex, weight and age, and thus in no way limits the scope of the present invention. Showing excellent in vivo persistency and titer, the pharmaceutical composition of the present invention may be remarkably decreased in administration frequency. Since the pharmaceutical composition of the present invention has excellent in vivo durability and stability with prolonged in vivo half-life, it can remarkably reduce the administration frequency and dose of the drugs.

In accordance with still a further aspect, the present invention provides a method for preventing or treating intestinal disease, intestinal injury, or gastrosis, comprising administering the long-acting GLP-2 conjugate in a therapeutically effective amount to a subject in need thereof.

As used herein, the term "administration" or "administering" refers to introduction of an effective ingredient into a patient in a suitable manner. As long as it allows the effective ingredient to reach a target tissue, any administration may be taken. Examples of the administration route include intraperitoneal, intravenous, intramuscular, subcutaneous, interdermal, oral, local, intranasal, intrapulmonary and intrarectal administration, but are not limited thereto. However, since peptides are digested upon oral administration, the effective ingredient of a composition for oral administration should be coated or formulated for protection against degradation in the stomach. Preferably, the effective ingredient may be formulated into an injection. In addition, the long-acting conjugate may be administered with the aid of any device that helps transmit the effective ingredient into target cells.

Examples of the subject to be treated include humans, apes, cow, horses, sheep, pigs, chickens, turkeys, quails, cats, dogs, mice, rats, rabbits and guinea pigs, but are not limited thereto. Preferred subjects are mammals, particularly humans.

The term "therapeutically effective amount", as used in the context of the effective ingredient, refers to an amount sufficient for preventing or treating a disease, that is, intestinal disease, intestinal injury, or gastrosis in a reasonable benefit/risk ratio so as to be applicable to medical treatment.

The long-acting GLP-2 conjugate of the present invention shows a prolonged in vivo half-life and an improved in vivo durability and stability. Thus, the long-acting GLP-2 conjugate of the present invention can be administered at a remarkably low dose and exhibit an improvement in drug compliance without fluctuation in blood glucose level. Accordingly, the long-acting GLP-2 conjugate of the present invention can be effectively used for preventing or treating intestinal disease, intestinal injury, or gastrosis.

MODE FOR INVENTION

The present invention is further illustrated by the following Examples. However, it shall be understood that these Examples are only used to specifically set forth the present invention, rather than being understood that they are used to limit the present invention in any form.

Example 1

Pegylation of Imidazo-Acetyl-GLP-2

Imidazo-acetyl GLP-2 (CA-GLP-2, A2G, 34C, American Peptide, U.S.A.) was reacted with 10K MAL-PEG-ALD PEG (heterobifunctional PEG having a maleimide and a aldehyde group at each end, NOF Inc., Japan), so as to pegylate the 34th cysteine residue (Cys34) of the CA-GLP-2. Here, the molar ratio of CA-GLP-2 to PEG was 1:3, and the reaction was performed at room temperature for 3 hours, with a peptide concentration of 3.5 mg/mL. Further, the reaction was carried out in a 50 mM Tris-HCl buffer in the presence of 20 mM sodium cyanoborohydride (SCB) as a reducing agent. After the reaction was completed, the resulting product, mono-pegylated CA-GLP-2-PEG complex was purified by chromatography using a SOURCE S column (LRC25, Pall Corporation) under the following conditions.

Column: SOURCE S (LRC25, Pall Corporation)

Flow rate: 4.0 ml/min

Gradient: eluent B 0% 5, Pall Corporation) by umM citric acid, pH 2.0+45% ethanol, B: A+1 M KCl)

Example 2

Preparation of Imidazo-Acetyl-GLP-2(A2G, 34C)-PEG-Immunoglobulin Fc Conjugate

The mono-pegylated CA-GLP-2 (A2G, 34C) complex purified above was mixed with an immunoglobulin (IgG) Fc fragment (Korean Patent No. 10-725315) at a molar ratio of 1:6, followed by reacting them at 4° C. for 20 hours, with a peptide concentration of 20 mg/ml. At this time, the reaction was performed in a 100 mM potassium phosphate buffer (pH 6.0) in the presence of 20 mM SCB as a reducing agent. After the reaction was completed, the reaction mixture was subjected to three-step chromatography using a SOURCE Phe column (XK16, GE Healthcare), a SOURCE 15Q column (LRC25, Pall Corporation) and a SOURCE ISO (HR16, GE Healthcare) column under the following conditions.

Column: SOURCE Phe (XK16, GE Healthcare)

Flow rate: 2.0 ml/min

Gradient: eluent B 100%) GE HealthcmM Tris, pH 8.0; B: A+2.6 M NaCl)

Column: SOURCE 15Q (LRC25, Pall Corporation)

Flow rate: 5.0 ml/min

Gradient: eluent B 0→30% for 120 min (A: 20 mM Tris-HCl, pH 8.0, B: A+1 M NaCl)

Column: SOURCE ISO (HR16, GE Healthcare)

Flow rate: 2.0 ml/min

Gradient: eluent B 100%, GE Healthcare) aCl) NamM Tris-HCl, pH 8.0, B: A+1.1 M ammonium sulfate)

Figure 2:
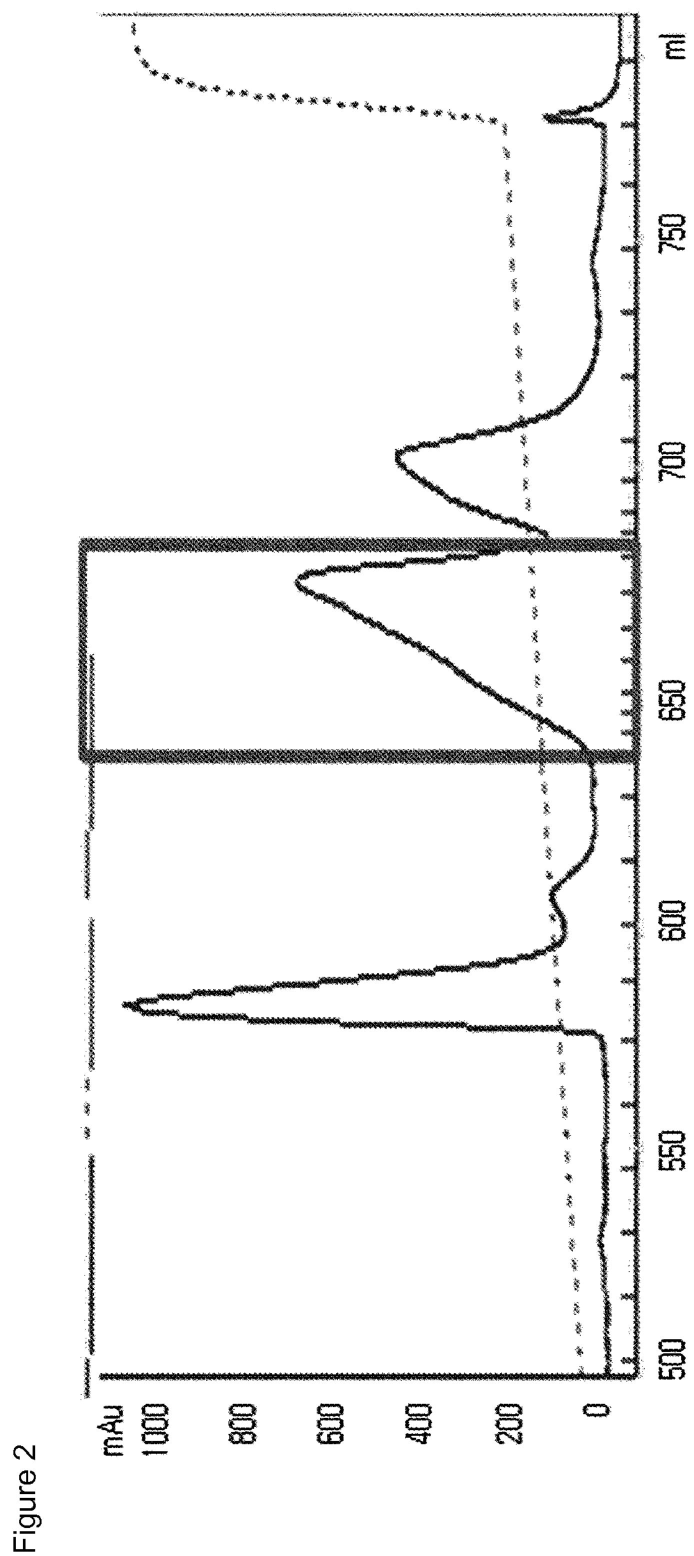
FIG. 2 shows the purification profile of a CA GLP-2(A2G, 34C)-10K PEG-immunoglobulin Fc conjugate, which is purified by using a Source 15Q column.
Figure 3:
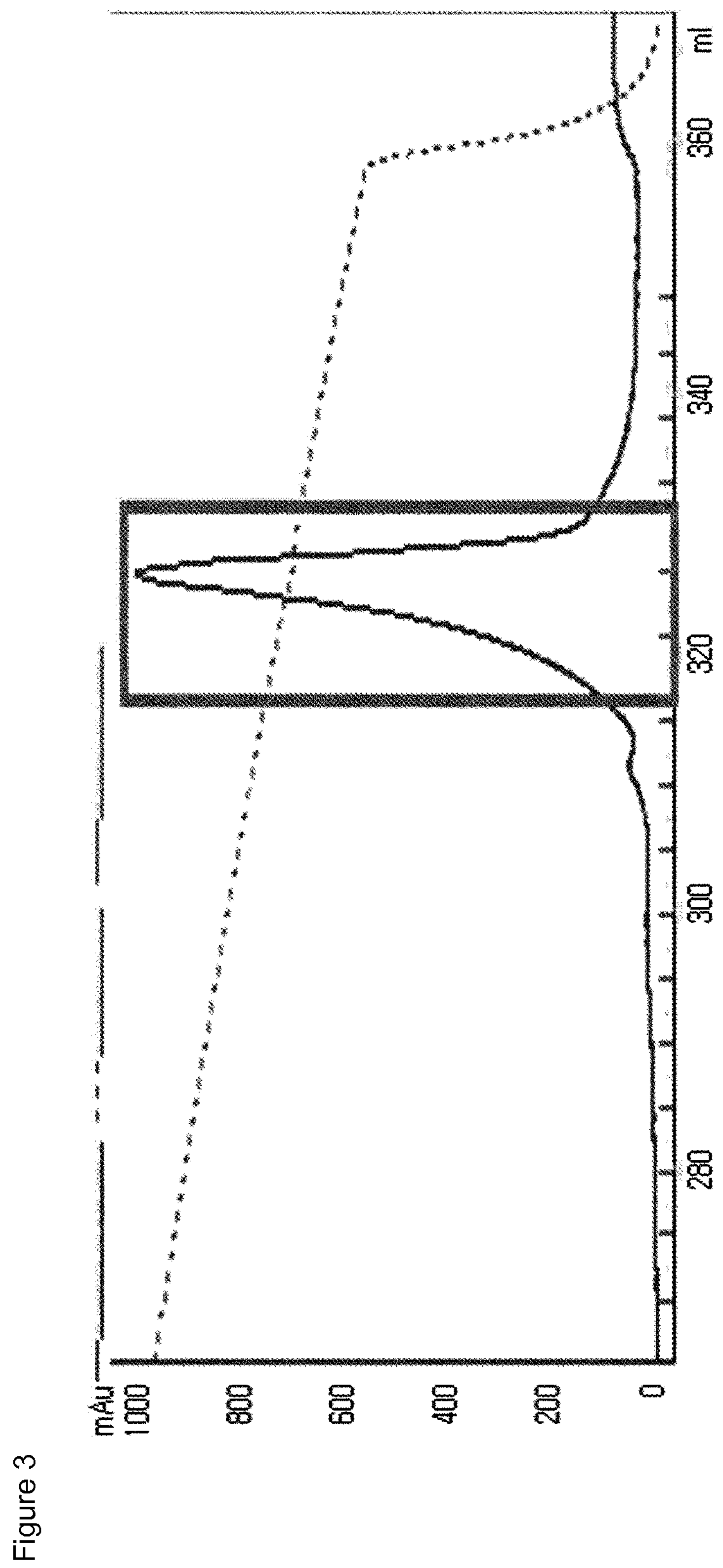
FIG. 3 shows the purification profile of a CA GLP-2(A2G, 34C)-10K PEG-immunoglobulin Fc conjugate, which is purified by using a Source ISO column.
Figure 4:
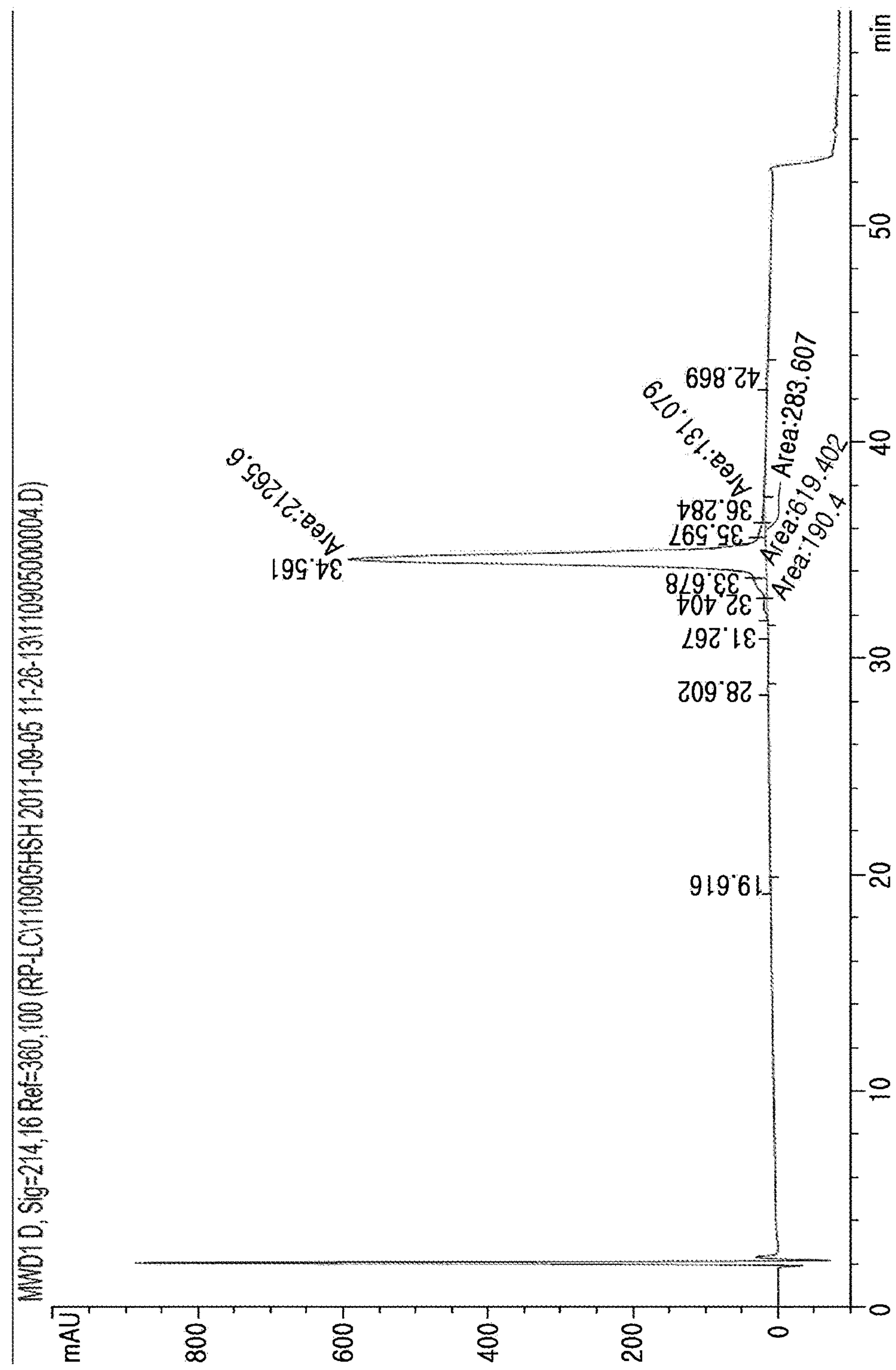
FIG. 4 shows the results of reverse phase HPLC for analyzing the purity of a CA GLP-2(A2G, 34C)-10K PEG-immunoglobulin Fc conjugate.

Each purification profile of the SOURCE Phe column, SOURCE 15Q column and SOURCE ISO column are shown in FIGS. 1, 2 and 3, respectively. As a result of reverse-phase HPLC analysis, the CA-GLP-2 (A2G, 34C)-10K PEG-Fc conjugate was purified with a purity of 94.2% (FIG. 4), and the yield thereof was 12.5%.

Example 3

Measurement of In Vitro Binding Affinity of CA-GLP-2 (A2G, 34C)-10K PEG-Fc Conjugate to GLP-2 Receptor In order to measure the efficacy of the CA-GLP-2 (A2G, 34C)-10K PEG-Fc conjugate (hereinafter, "GLP-2 conjugate") prepared in Example 2, a method for measuring in vitro cell activity was used as follows. In this method, a Chinese hamster ovary (CHO) cell line, CHO/hGLP-2R being transformed to express a gene encoding human GLP-2 receptor was employed.

The CHO/hGLP-2R cells were sub-cultured 2 to 3 times a week, and were seeded on a 96-well plate at a concentration of $1\times10^5$ cells/well, followed by culturing for 24 hours. The thus cultured CHO/hGLP-2R cells were treated with native GLP-2 at a concentration of 1000 to 0.002 nM; a long-acting formulation of native GLP-2 (GLP-2-PEG-Fc conjugate, LAPS-GLP-2) at a concentration of 10000 to 0.02 nM; a long-acting formulation of a GLP-2 derivative via lysine-specific conjugation (LAPS-DA-GLP-2, LAPS-CA-GLP-2, LAPS-OH-GLP-2) at a concentration of 10000 to 0.02 nM; and a long-acting formulation of a GLP-2 derivative via C-terminal cysteine-specific conjugation (LAPS-CA-GLP-2 (A2G, 34C)) at a concentration of 10000 to 0.02 nM, respectively. The intracellular level of cAMP, as a second messenger used for signal transduction, in the CHO/hGLP-2R cells treated with each compound was measured by using a cAMP assay kit (MD, USA), and assayed for luciferase activity by a VICTOR LIGHT luminometer (PerkinElmer Life Sciences). The $EC_{50}$ value of each compound was also measured.

Figure 5:
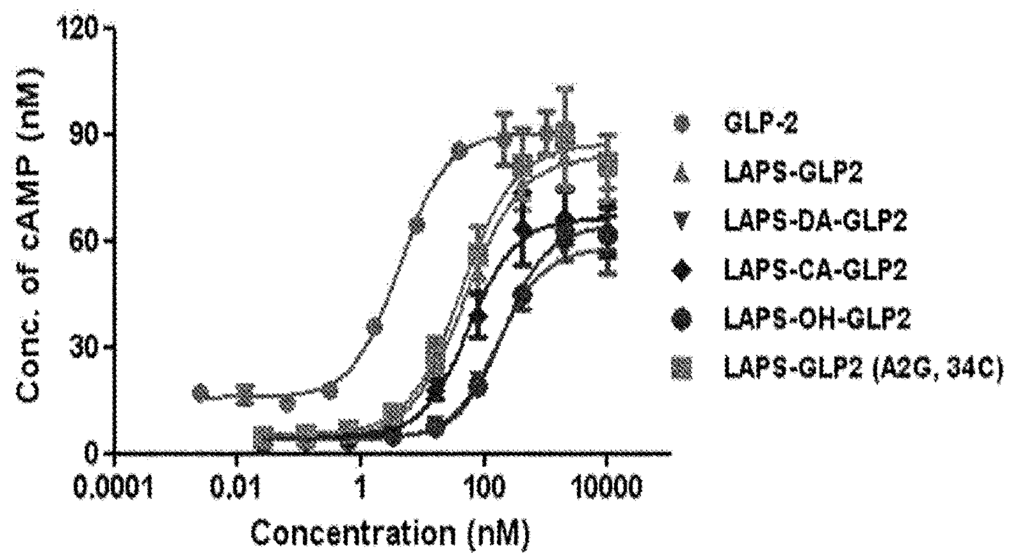
FIG. 5 shows the in vitro results of measuring binding affinities to a GLP-2 receptor of the GLP-2 derivative and a native GLP-2.

As shown in FIG. 5, the long-acting formulation of the GLP-2 derivative via lysine-specific conjugation (LAPS-DA-GLP-2, LAPS-CA-GLP-2, LAPS-OH-GLP-2) showed lower in vitro activity than the long-acting formulation of native GLP-2 (LAPS-GLP-2) (2.6-7.5% vs 8.6%). In contrast, the long-acting formulation of the GLP-2 derivative via C-terminal cysteine-specific conjugation (LAPS-CA-GLP-2 (A2G, 34C)) showed higher in vitro activity than the long-acting formulation of native GLP-2 (LAPS-GLP-2) (9.9% as compared with native GLP-2).

These results have confirmed that the GLP-2 conjugate, in which one end of the non-peptidyl polymer is covalently linked to the C-terminal of the GLP-2 derivative and the other end thereof is covalently linked to the immunoglobulin Fc fragment, shows an enhanced binding affinity to a GLP-2 receptor as compared with the previous GLP-2 conjugate, thereby extending an in vivo half-life and improving an in vivo durability and stability Specific terms used in the present description are given only to describe specific embodiments and are not intended to limit the present invention. Singular forms used in the present description include plural forms unless they apparently represent opposite meanings. The meaning of "including" or "having" used in the present description is intended to embody specific properties, regions, integers, steps, operations, elements and/or components, but is not intended to exclude presence or addition of other properties, regions, integers, steps, operations, elements, components and/or groups.

INDUSTRIAL APPLICABILITY

The GLP-2 conjugate of the present invention has remarkably high binding affinity for a GLP-2 acceptor, thereby showing long-lasting in vivo therapeutic efficacy and prolonged in vivo half-life. Therefore, the GLP-2 conjugate of the present invention can be effectively used for the treatment or prevention of intestinal disease, intestinal injury or gastrosis with remarkably low administration frequency.

The invention claimed is:

1. A glucagon-like peptide-2 (GLP-2) conjugate comprising native GLP-2 or its derivative and an immunoglobulin Fc fragment being covalently linked via a non-peptidyl polymer, wherein the native GLP-2 or its derivative has a thiol group introduced at its C-terminal end, and one end of the non-peptidyl polymer is linked to the C-terminal thiol group of the GLP-2 or its derivative, wherein the derivative of GLP-2 is selected from the group consisting of a GLP-2 derivative prepared by removing α-carbon of histidine which is the first amino acid at the N-terminal end of the native GLP-2 and an N-terminal amine group bound thereto; a GLP-2 derivative prepared by deleting an N-terminal amine group of the native GLP-2; a GLP-2 derivative prepared by substituting an N-terminal amine group of the native GLP-2 with a hydroxyl group; a GLP-2 derivative prepared by modifying an N-terminal amine group of the native GLP-2 with a dimethyl group; and a GLP-2 derivative prepared by substituting an N-terminal amine group of the native GLP-2 with a carboxyl group.

2. The GLP-2 conjugate according to claim 1, wherein the thiol group of the GLP-2 or its derivative is introduced by binding cysteine to the C-terminal end thereof.

3. The GLP-2 conjugate according to claim 1, wherein the non-peptidyl polymer covalently linked to the thiol group of the GLP-2 or its derivative.

4. The GLP-2 conjugate according to claim 1, wherein the non-peptidyl polymer is selected from the group consisting of polyethylene glycol, polypropylene glycol, a copolymer of ethylene glycol and propylene glycol, polyoxyethylated polyol, polyvinyl alcohol, polysaccharides, dextran, polyvinyl ethyl ether, biodegradable polymer, lipid polymer, chitin, hyaluronic acid, and a combination thereof.

5. The GLP-2 conjugate according to claim 1, wherein the non-peptidyl polymer has a reactive group selected from the group consisting of an aldehyde group, a propionic aldehyde group, a butyl aldehyde group, a maleimide group and a succinimide group at both terminal ends thereof.

6. The GLP-2 conjugate according to claim 5, wherein the succinimide group is selected from the group consisting of succinimidyl propionate, succinimidyl carboxymethyl, hydroxy succinimidyl and succinimidyl carbonate.

7. The GLP-2 conjugate according to claim 5, wherein the non-peptidyl polymer has a maleimide group at one terminal end and an aldehyde group at the other terminal end.

8. The GLP-2 conjugate according to claim 1, wherein the immunoglobulin Fc fragment is non-glycosylated.

9. The GLP-2 conjugate according to claim 8, wherein the immunoglobulin Fc fragment further comprises a hinge region.

10. The GLP-2 conjugate according to claim 1, wherein the immunoglobulin Fc fragment is an IgG4 Fc fragment.

11. The GLP-2 conjugate according to claim 10, wherein the immunoglobulin Fc fragment is a human non-glycosylated IgG4 Fc fragment.

12. A method for preparing the GLP-2 conjugate according to claim 1, comprising:

1) covalently linking a non-peptidyl polymer having a reactive group selected from the group consisting of aldehyde, maleimide and succinimide derivatives at both terminal ends to a thiol group of a GLP-2 or its derivative, wherein the GLP-2 or its derivative has a thiol group introduced at its C-terminal end;
2) isolating a complex, in which the non-peptidyl polymer is covalently linked to the C-terminal thiol group of the GLP-2 or its derivative, from the reaction mixture of Step (1);
3) covalently linking the other end of the non-peptidyl polymer in the complex to an immunoglobulin Fc fragment; and
4) isolating a GLP-2 conjugate, in which both ends of the non-peptidyl polymer are linked to the immunoglobulin Fc fragment and GLP-2 or its derivative, respectively, from the reaction mixture of Step 3).

13. The method according to claim 12, wherein the non-peptidyl polymer in Step (1) is covalently linked to the C-terminal thiol group of the GLP-2 or its derivative.

14. The method according to claim 12, wherein the GLP-2 or its derivative and non-peptidyl polymer in Step (1) are reacted at a molar ratio of 1:2 to 1:10 under the condition of pH 2 to 4.

15. A pharmaceutical composition comprising the GLP-2 conjugate according to claim 1 as an active ingredient.

16. A method for treating an intestinal disease, comprising administering the GLP-2 conjugate of claim 1 to a patient in need thereof.

* * * * *

SEQUENCE LISTING

<160> NUMBER OF SEQ ID NOS: 1

<210> SEQ ID NO 1
<211> LENGTH: 33
<212> TYPE: PRT
<213> ORGANISM: Homo sapiens

<400> SEQUENCE: 1

His Ala Asp Gly Ser Phe Ser Asp Glu Met Asn Thr Ile Leu Asp Asn
1 5 10 15

Leu Ala Ala Arg Asp Phe Ile Asn Trp Leu Ile Gln Thr Lys Ile Thr
20 25 30

Asp